US012521275B1

(12) United States Patent
Brooke

(10) Patent No.: US 12,521,275 B1
(45) Date of Patent: Jan. 13, 2026

(54) HAND WARMING DEVICE

(71) Applicant: Patrick Alan Brooke, Mandan, ND (US)

(72) Inventor: Patrick Alan Brooke, Mandan, ND (US)

(*) Notice: Subject to any disclaimer, the term of this patent is extended or adjusted under 35 U.S.C. 154(b) by 0 days.

(21) Appl. No.: 18/435,445

(22) Filed: Feb. 7, 2024

(51) Int. Cl.
*A61F 7/00* (2006.01)
*H05B 3/06* (2006.01)

(52) U.S. Cl.
CPC ............... *A61F 7/007* (2013.01); *H05B 3/06* (2013.01); *A61F 2007/0036* (2013.01); *A61F 2007/0037* (2013.01); *A61F 2007/0038* (2013.01)

(58) Field of Classification Search
CPC ............................................... A61F 2007/0036
See application file for complete search history.

(56) References Cited

U.S. PATENT DOCUMENTS 4,088,324 A * 5/1978 Farmer .............. A63B 69/3632 273/DIG. 26
5,729,864 A * 3/1998 Lie ......................... A63B 60/08 16/DIG. 12
5,746,661 A * 5/1998 Murphy ............... A63B 53/007 473/294
6,968,599 B2 * 11/2005 Blauer ................... A45C 13/26 81/177.1
6,998,576 B2 * 2/2006 Marquis .................. B25G 1/00 219/541
10,986,885 B1 4/2021 Von Behren
2008/0053979 A1 3/2008 Toya
2023/0239971 A1 7/2023 Schultz
2023/0404796 A1 12/2023 Zhu

FOREIGN PATENT DOCUMENTS

CN 213250265 5/2021
CN 219439661 8/2023
WO 2015027488 3/2015
WO 2023051629 4/2023

* cited by examiner

*Primary Examiner* — Kaitlyn E Smith
(74) *Attorney, Agent, or Firm* — Jeffrey A. Proehl; Woods, Fuller, Shultz & Smith, P.C.

(57) ABSTRACT

A hand warming device for warming a hand of a user gripping the device may comprise a housing having an exterior surface, a heating element to heating the exterior surface, a power source, and a power switch. The exterior surface may be contoured to facilitate contact between the exterior surface and the hand of the user when the housing is held by a clenched fist of the user. The housing may be elongated along a first axis between opposite first and second ends. The exterior surface of the housing has a shape having a longitudinal profile taken in a longitudinal plane extending along the first axis. The longitudinal profile may have an inner boundary and an outer boundary extending between the ends, and the longitudinal profile may be generally comma-shaped.

19 Claims, 3 Drawing Sheets

HAND WARMING DEVICE

BACKGROUND

Field

The present disclosure relates to body warming devices and more particularly pertains to a new hand warming device for transferring heat to the hand of a person in a highly effective manner by maximizing the opportunity for contact between the device and the person's hand.

SUMMARY

In some aspects, the present disclosure relates to a hand warming device for warming a hand of a user gripping the device. The device may comprise a housing having a housing interior and an exterior surface, and a heating element configured to cause heating of the exterior surface of the housing for transferring heat to the hand of the user gripping the exterior surface of the housing. The device may also comprise a power source configured to supply electrical power to the heating element and a power switch for configured to control the supply of electrical power from the power source to the heating element. The exterior surface of the housing wall may be contoured to facilitate contact between the exterior surface and a palm side of a central portion of the hand and inner sides of fingers and thumb of the hand when the housing is held by a clenched fist of the user. The housing may be elongated along a first axis between opposite first and second ends, and the exterior surface of the housing has a shape. The shape may have a longitudinal profile taken in a longitudinal plane extending along the first axis, and the longitudinal profile may have an inner boundary extending between the ends and an outer boundary extending between the ends. The longitudinal profile may be generally comma-shaped.

There has thus been outlined, rather broadly, some of the more important elements of the disclosure in order that the detailed description thereof that follows may be better understood, and in order that the present contribution to the art may be better appreciated. There are additional elements of the disclosure that will be described hereinafter and which will form the subject matter of the claims appended hereto.

In this respect, before explaining at least one embodiment or implementation in greater detail, it is to be understood that the scope of the disclosure is not limited in its application to the details of construction and to the arrangements of the components set forth in the following description or illustrated in the drawings. The disclosure is capable of other embodiments and implementations and is thus capable of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present disclosure. It is important, therefore, that the claims be regarded as including such equivalent constructions insofar as they do not depart from the spirit and scope of the present disclosure.

The advantages of the various embodiments of the present disclosure, along with the various features of novelty that characterize the disclosure, are disclosed in the following descriptive matter and accompanying drawings.

BRIEF DESCRIPTION OF THE DRAWINGS

The disclosure will be better understood and when consideration is given to the drawings and the detailed description which follows. Such description makes reference to the annexed drawings wherein.

DETAILED DESCRIPTION

Figure 1:
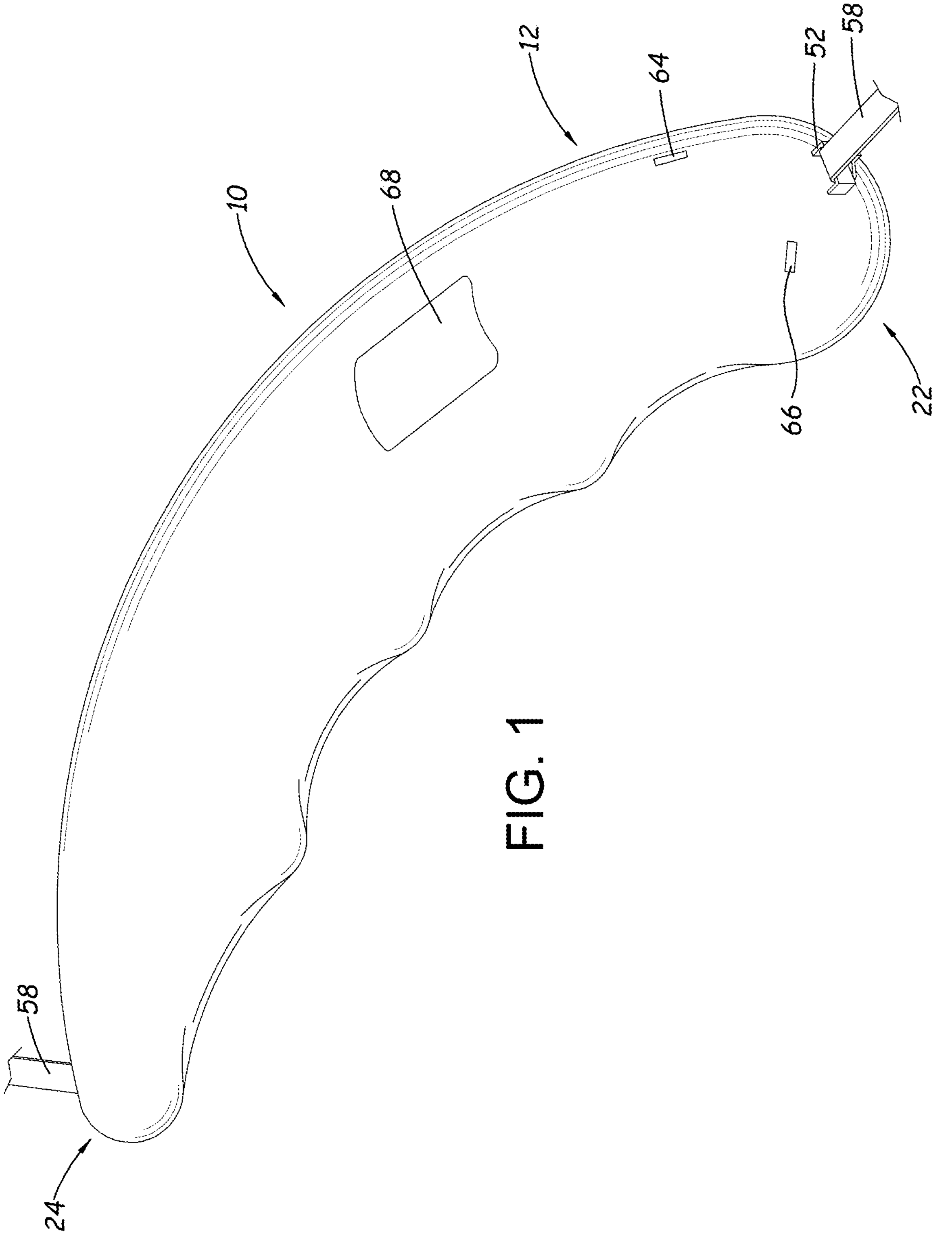
FIG. 1 is a schematic perspective view of a new hand warming device according to the present disclosure.
Figure 2:
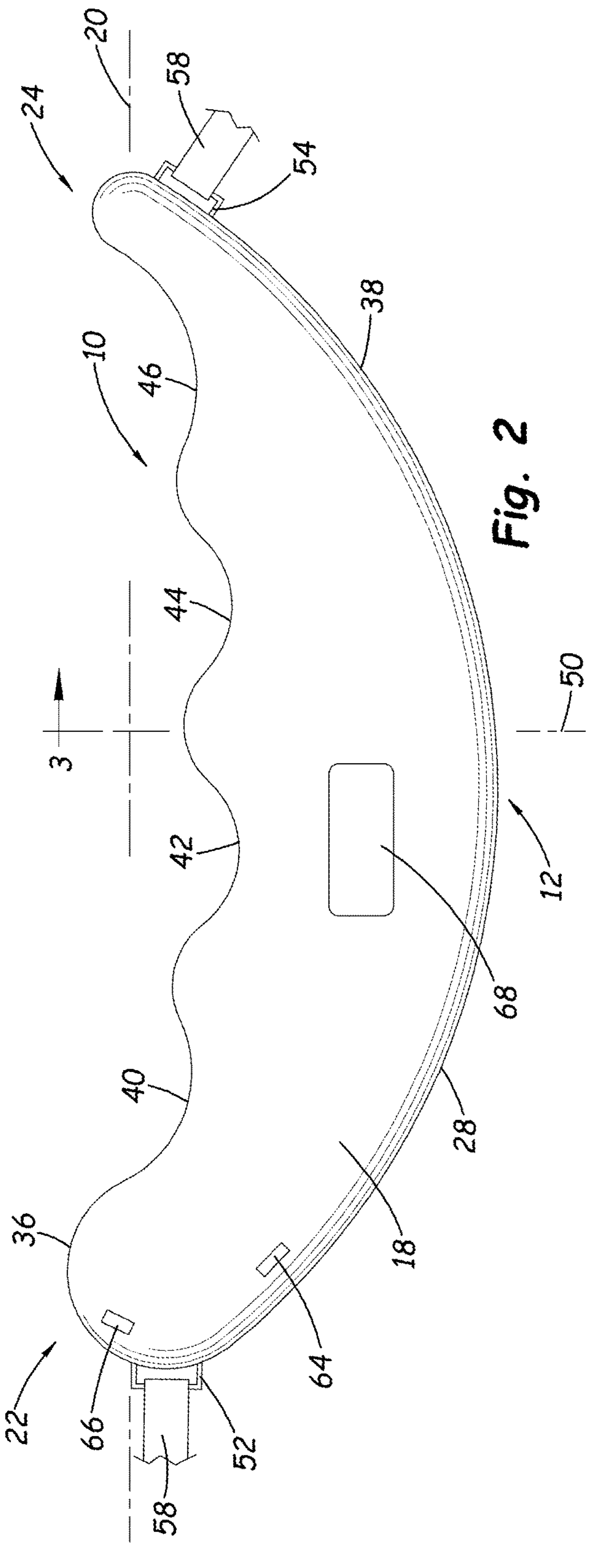
FIG. 2 is a schematic side view of the hand warmer, according to an illustrative embodiment.
Figure 3:
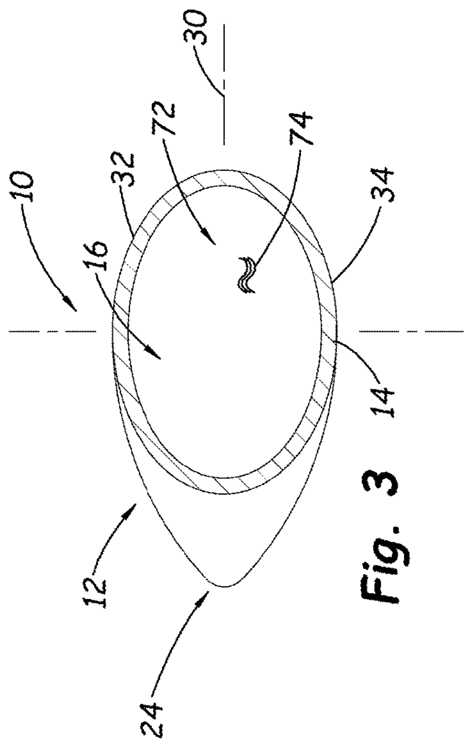
FIG. 3 is a schematic sectional view of the hand warmer taken along line 3-3 of FIG. 2, according to an illustrative embodiment.
Figure 4:
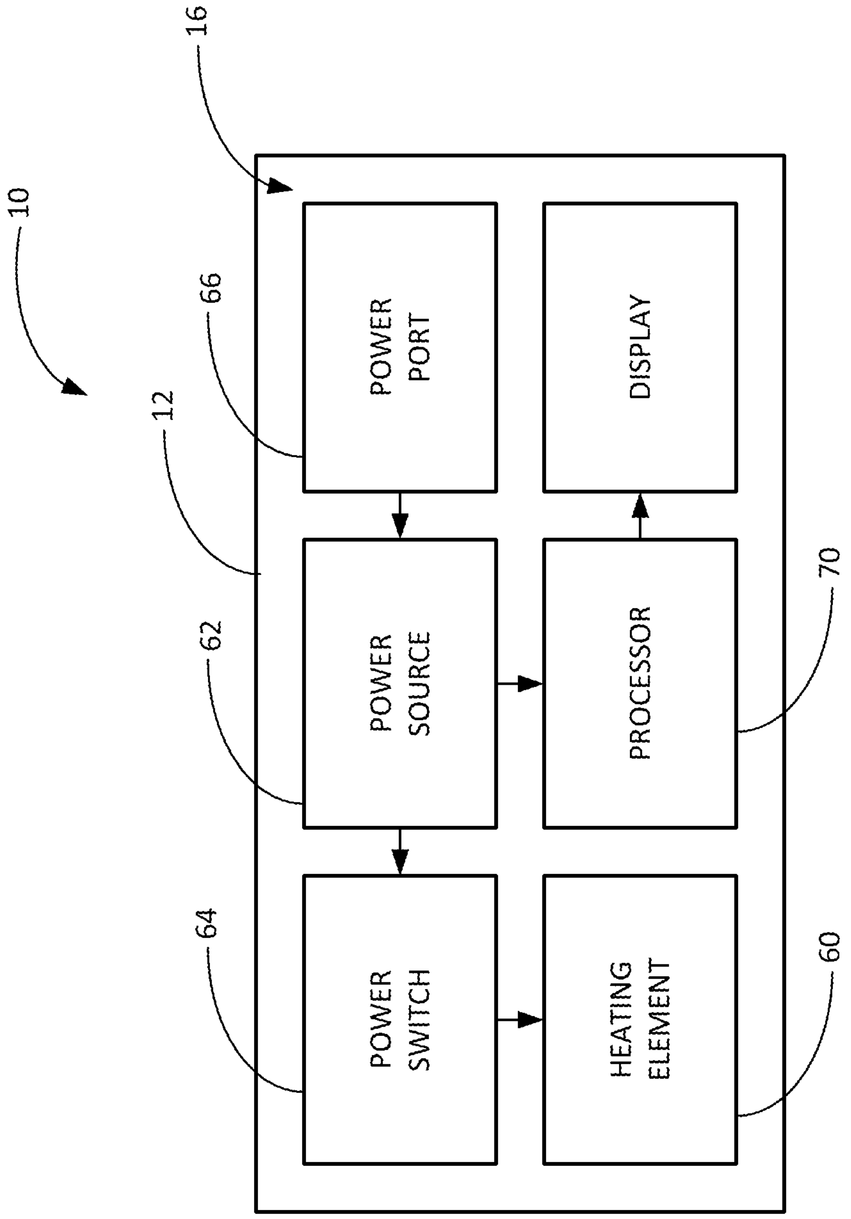
FIG. 4 is a schematic diagram of elements of the hand warmer, according to an illustrative embodiment.

With reference now to the drawings, and in particular to FIGS. 1 through 4 thereof, a new hand warming device embodying the principles and concepts of the disclosed subject matter will be described.

The disclosure generally relates to a hand warming device 10 which may be utilized for warming or transferring warmth to the hand of a user of the device, particularly when the user is gripping the device with a hand. For the purposes of this description, the hand has a central portion, a plurality of fingers radiating from the central portion, and a thumb also radiating from the central portion. The central portion has a palm side or surface, while the fingers and the thumb each have an inner side or surface.

The hand warming device 10 includes a housing 12 which may be gripped by the hand. The housing 12 has a housing wall 14 and a housing interior 16, with the housing wall extending about, and typically enclosing, the housing interior. The housing 12 has an exterior surface 18 which is contacted by the sides or surfaces of the hand of the user when the user is gripping the device 10. Typically, the exterior surface 18 is formed by the housing wall. In some optional embodiments, at least a portion of the exterior surface 18 is resiliently compressible, and this may be accomplished, for example, by covering some or all portions of the housing wall 14 with a foam material or an elastomeric material.

A significant feature of the device of the disclosure is the contouring of the exterior surface 18 of the housing wall in a manner that facilitates contact between the surface 18 and the hand of the user, such as the palm side of the central portion of the hand and the inner sides of the fingers and the thumb of the hand, particularly when the housing is held by a clenched fist formed by the central portion and the fingers of the hand. Optionally, somewhat different shape configurations of the exterior surface 18 may be optimized for left-hand and right-hand versions.

In general, the housing 12 may be elongated along a first axis 20 such that the housing has ends, including a first end 22 and a second end 24. The exterior surface 18 of the housing has an overall shape, which may have a longitudinal profile 28 that is taken in a longitudinal plane 30 extending along the first axis 20. The longitudinal profile 28 may be defined by the line at which the exterior surface 18 intersects the longitudinal plane 30.

In embodiments, the longitudinal profile 28 may be generally crescent-shaped, and the profile 28 may be generally comma-shaped to facilitate the fit of the exterior surface 18 in the fist of the user. Illustratively, the longitudinal profile 18 may be generally bulbous and blunt at the first end 22 of the housing, and may taper and be generally pointed at the second end 24 of the housing.

The shape of the exterior surface 18 may have opposite faces that are separated by the longitudinal plane 30, and may include a first face 32 and a second face 34. In embodiments, the first 32 and second 34 faces are substantially mirror images of each other. The longitudinal profile 28 may also have an inner boundary 36 and an outer boundary 38, and each of the boundaries may extend between the ends 22, 24. Illustratively, the inner boundary 36 has a shorter extent or length than the extent or length of the outer boundary 38. In illustrative embodiments, the outer boundary 38 may be arcuate to engage the palm side of the hand. The inner boundary 36 may have more contours than the outer boundary, and may be scalloped to engage the inner sides of the individual fingers of the hand. Illustratively, the inner boundary 36 may include a plurality of clefts 40, 42, 44, 46. The clefts may extend laterally with respect to the longitudinal plane 30. Illustratively, the clefts may be substantially uniformly spaced from each other and uniformly distributed between the ends 22, 24. Optionally, the plurality of clefts may comprise four clefts such that each of the fingers of the hand has an accommodating cleft.

The shape may also have a lateral cross section taken in a lateral plane 50 that is oriented perpendicular to the longitudinal plane 30. The intersection of the first face 32 with the lateral plane 50 may be generally arcuate in shape and similarly the intersection of the second face 34 with the lateral plane may also be generally arcuate.

In some embodiments, the housing 12 includes at least one securing loop 52 that is positioned on the housing wall 14, and may protrude from the exterior surface 18. The securing loop 52 may be positioned on the housing 12 toward one of the ends of the exterior surface. Further, a securing lanyard or strap 58 may be provided on the housing for assisting in securing the housing on the hand of the user. In embodiments, opposite ends of the securing strap 58 may be attached to the securing loop 52 on the housing to form a loop through which a portion of the hand may be inserted. Optionally, the securing strap 58 may be formed of an elastomeric material. As a further option, the strap 58 may be utilized to releasably connect a pair of the devices together, such as left-hand and right-hand versions of the device 10.

In further embodiments, a pair of the securing loops 52, 54 may be provided on the housing and may be located toward the opposite ends of the housing. The securing strap 58 may be attached to and extend between the pair of securing loops 52, 54 such that the housing 12 and the strap 58 form a continuous loop into which a portion of the hand may be inserted so that the housing is positioned along palm side of the hand and the strap 58 is positioned along the backside of the central portion of the hand.

The hand warming device 10 may also include a heating element 60 to cause or produce heating of the exterior surface 18 of the housing for transferring the heat to the hand of the user when the user is gripping the exterior surface of the housing. The heating element 60 may be activated or operated by electrical power, and the heating element may generate heat by electrical resistance. The heating element 60 may be at least partially positioned in the housing interior, and/or may be integrated into at least a portion of the housing wall. The device 10 may also include a power source 62 for supplying electrical power to the heating element 60. The power source 62 may be located in the housing interior 16. The power source 62 may comprise a battery, and the battery may be rechargeable and/or may be replaceable in the housing. The device 10 may have a power switch 64 for controlling the supply of electrical power from the power source 62 to the heating element 60. The power switch 64 may be accessible at the exterior surface 18 of the housing, and may be located toward the first end 22 of the housing which may facilitate the accessibility of the switch by, for example, the thumb when the housing is grasped by the hand of the user. For example, the power switch 64 may be a switch which is slid between "ON" and "OFF" positions, or may be a momentary button switch. The device 10 may further include a port 66 for receiving electrical power from a source exterior to the device, such as for supplying power to the heating element either directly or via a power source. The port 66 may be in electrical communication with the power source to supply power to, for example, a rechargeable battery for recharging the battery. The port 66 may have any suitable configuration, and one example is a jack based upon a standard such as the universal serial bus (USB) standard.

The device 10 may have an information display 68 which is configured to display characters or graphics, and may be positioned on the exterior surface 18 of the housing. Processing circuitry 70 may be provided for the device, and the circuitry may be in communication with the information display 68 and the power source 62 to generate a signal to send to the display 68 to cause the display to communicate information. The processing circuitry 70 may be located in the housing interior 16, and may comprise a microprocessor. The display 68 and processing circuitry 70 may form a number of functions, such as indicating the current operational status of the device (e.g., "ON" or "OFF"), indicating the current time, indicating the current temperature, or providing a timer capability.

In some embodiments, the housing interior 16 may define a cavity 72, and the cavity may be filled with a gelatinous material 74 which has a characteristic of retaining and/or maintaining a temperature level. For example, the material 74 may be configured to retain heat, so that heat generated by the heating element may be better retained by the device. The material 74 may additionally, or alternatively, be configured to retain cold, so that the device may be refrigerated to cool the material, and the device may subsequently gripped by the user to cool the hand.

It should be appreciated that in the foregoing description and appended claims, that the terms "substantially" and "approximately," when used to modify another term, mean "for the most part" or "being largely but not wholly or completely that which is specified" by the modified term.

It should also be appreciated from the foregoing description that, except when mutually exclusive, the features of the various embodiments described herein may be combined with features of other embodiments as desired while remaining within the intended scope of the disclosure.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated.

With respect to the above description then, it is to be realized that the optimum dimensional relationships for the parts of the disclosed embodiments and implementations, to include variations in size, materials, shape, form, function and manner of operation, assembly and use, are deemed readily apparent and obvious to one skilled in the art in light of the foregoing disclosure, and all equivalent relationships to those illustrated in the drawings and described in the specification are intended to be encompassed by the present disclosure.

Therefore, the foregoing is considered as illustrative only of the principles of the disclosure. Further, since numerous modifications and changes will readily occur to those skilled in the art, it is not desired to limit the disclosed subject matter to the exact construction and operation shown and described, and accordingly, all suitable modifications and equivalents may be resorted to that fall within the scope of the claims.

I claim:

1. A hand warming device for warming a hand of a user gripping the device, the device comprising:

a housing for being gripped by the hand of the user, the housing having a housing interior and an exterior surface for contacting the hand of the user;

a heating element configured to cause heating of the exterior surface of the housing for transferring heat to the hand of the user gripping the exterior surface of the housing;

a power source configured to supply electrical power to the heating element; and a power switch configured to control the supply of electrical power from the power source to the heating element;

wherein the exterior surface of the housing is contoured to facilitate contact between the exterior surface and a palm side of a central portion of the hand and inner sides of fingers and thumb of the hand when the housing is held by a clenched fist of the user;

wherein the housing is elongated along a first axis between opposite first and second ends, the first and second ends forming furthest opposite extents terminations of the housing, the exterior surface of the housing having a shape, the shape having a longitudinal profile taken in a longitudinal plane extending along the first axis;

wherein both of the opposite ends of the housing are closed;

wherein the longitudinal profile has an inner boundary extending between the first and second ends, the inner boundary being scalloped with a plurality of clefts for each engaging the inner side of the individual fingers of the hand of the user to facilitate contact between the exterior surface of the housing and the individual fingers of the hand and heat transfer from the exterior surface to the hand; and wherein the longitudinal profile has an outer boundary opposite of the inner boundary and extending between the first and second ends, the outer boundary being arcuate to engage the palm side of the hand to facilitate contact between the exterior surface of the housing and the palm side of the hand and heat transfer from the exterior surface to the hand.

2. The device of claim 1 wherein the inner boundary is generally concave between the first and second ends in the longitudinal plane and is scalloped from the first end to the second end of the housing; and wherein the outer boundary is convex between the first and second ends in the longitudinal plane and arcuate from the first end to the second end.

3. The device of claim 1 wherein each of the clefts of the plurality of clefts extend laterally with respect to the longitudinal plane.

4. The device of claim 3 wherein the clefts of the plurality of clefts are substantially uniformly distributed between the ends.

5. The device of claim 1 wherein the inner boundary has a shorter extent in the longitudinal plane than the outer boundary in the longitudinal plane such that the longitudinal profile is generally comma-shaped.

6. The device of claim 1 wherein the longitudinal profile tapers from a substantially bulbous said first end of the housing to a substantially pointed said second end of the housing such that the bulbous first end and the pointed second end form the furthest opposite extents of the housing.

7. The device of claim 1 wherein the shape of the exterior surface has a lateral cross section taken in a lateral plane oriented perpendicular to the longitudinal plane, the shape having opposite faces separated by the longitudinal plane, the intersection of the first face with a lateral plane being substantially ovular.

8. The device of claim 1 wherein the housing includes at least one securing loop extending from a housing wall of the housing; and wherein the device additionally comprises a securing strap attached to the at least one securing loop for extending about a central portion of the hand of the user.

9. The device of claim 1 additionally comprising a port on the housing for receiving electrical power from a source exterior to the device, the port being in electrical communication with the power source to supply the power to the power source for recharging the power source.

10. The device of claim 1 additionally comprising an information display positioned on the exterior surface of the housing and configured to display characters; and processing circuitry in communication with the information display and the power source to generate a signal to send to the information display, the processing circuitry being located in the housing interior, the processing circuitry including a microprocessor.

11. The device of claim 1 wherein at least a portion of the exterior surface of the housing is resiliently compressible.

12. The device of claim 1 wherein the housing interior defines a cavity, the cavity being filled with a gelatinous material with a characteristic for maintaining a temperature level.

13. The device of claim 1 additionally comprising:

a port on the housing for receiving electrical power from a source exterior to the device, the port being in electrical communication with the power source to supply the power to the power source for recharging the power source;

an information display positioned on the exterior surface of the housing and configured to display characters;

processing circuitry in communication with the information display and the power source to generate a signal to send to the information display, the processing circuitry being located in the housing interior, the processing circuitry including a microprocessor;

wherein at least a portion of the exterior surface of the housing is resiliently compressible; and wherein the housing interior defines a cavity, the cavity being filled with a gelatinous material with a characteristic for maintaining a temperature level.

14. A hand warming device for warming a hand of a user gripping the device, the device comprising:

a housing for being gripped by the hand of the user, the housing having a housing interior and an exterior surface for contacting the hand of the user;

a heating element configured to cause heating of the exterior surface of the housing for transferring heat to the hand of the user gripping the exterior surface of the housing;

a power source configured to supply electrical power to the heating element; and a power switch configured to control the supply of electrical power from the power source to the heating element;

wherein the exterior surface of the housing is contoured to facilitate contact between the exterior surface and a palm side of a central portion of the hand and inner sides of fingers and thumb of the hand when the housing is held by a clenched fist of the user;

wherein the housing is elongated along a first axis between opposite first and second ends, the first and second ends forming furthest opposite extents terminations of the housing, the exterior surface of the housing having a shape, the shape having a longitudinal profile taken in a longitudinal plane extending along the first axis;

wherein both of the opposite ends of the housing are closed, the longitudinal profile being narrower at the opposite first and second ends and wider between the opposite ends;

wherein the longitudinal profile has an inner boundary extending between the first and second ends, the inner boundary being scalloped with a plurality of clefts for each engaging the inner side of the individual fingers of the hand of the user to facilitate contact between the exterior surface of the housing and the individual fingers of the hand and heat transfer from the exterior surface to the hand; and wherein the longitudinal profile has an outer boundary extending between the first and second ends, the outer boundary being located opposite of the inner boundary with respect to the first axis, the outer boundary being arcuate to engage the palm side of the hand to facilitate contact between the exterior surface of the housing and the palm side of the hand and heat transfer from the exterior surface to the hand;

wherein the inner boundary is scalloped from the first end to the second end of the housing and the outer boundary is a continuous arc from the first end to the second end of the housing;

wherein the clefts are substantially uniformly distributed between the first and second ends, each of the clefts extending laterally with respect to the longitudinal plane; and wherein the longitudinal profile tapers from a substantially bulbous said first end of the housing to a substantially pointed said second end of the housing.

15. The device of claim 14 wherein the shape of the exterior surface of the housing has a lateral cross section taken in a lateral plane oriented perpendicular to the longitudinal plane, the shape having opposite faces separated by the longitudinal plane, the intersection of the first face with a lateral plane being substantially ovular.

16. The device of claim 14 wherein the housing includes at least one securing loop extending from a housing wall of the housing; and wherein the device additionally comprises a securing strap attached to the at least one securing loop for extending about a central portion of the hand of the user.

17. The device of claim 14 additionally comprising a port on the housing for receiving electrical power from a source exterior to the device, the port being in electrical communication with the power source to supply the power to the power source for recharging the power source.

18. The device of claim 14 wherein at least a portion of the exterior surface of the housing is resiliently compressible.

19. The device of claim 14 wherein the housing interior defines a cavity, the cavity being filled with a gelatinous material with a characteristic for maintaining a temperature level.

* * * * *